(12) United States Patent
Bhargav et al.

(10) Patent No.: US 9,681,909 B2
(45) Date of Patent: Jun. 20, 2017

(54) TREATMENT DEVICES AND METHODS

(75) Inventors: Shaily Bhargav, Mountian View, CA (US); David A. Blau, Cupertino, CA (US); James G. Lovewell, San Leandro, CA (US); Robert M. Pearson, San Jose, CA (US)

(73) Assignee: AngioDynamics, Inc.

( * ) Notice: Subject to any disclaimer, the term of this patent is extended or adjusted under 35 U.S.C. 154(b) by 778 days.

(21) Appl. No.: 12/489,817

(22) Filed: Jun. 23, 2009

(65) Prior Publication Data

US 2009/0318905 A1    Dec. 24, 2009

Related U.S. Application Data

(60) Provisional application No. 61/074,853, filed on Jun. 23, 2008.

(51) Int. Cl.
*A61B 18/12* (2006.01)

(52) U.S. Cl.
CPC .. *A61B 18/1206* (2013.01); *A61B 2018/1273* (2013.01)

(58) Field of Classification Search
CPC ....... A61B 18/04; A61B 18/082; A61B 18/10; A61B 18/12; A61B 18/1206; A61B 18/1233; A61B 18/14; A61B 18/1477; A61B 2018/00577; A61B 2018/00642; A61B 2018/00702; A61B 2018/00827;

(Continued)

(56) References Cited

U.S. PATENT DOCUMENTS 1,653,819 A    12/1927  Northcott et al.
4,016,886 A     4/1977  Doss
(Continued)

FOREIGN PATENT DOCUMENTS

DE    863111      1/1953
DE    4000893     7/1991
(Continued)

OTHER PUBLICATIONS

Amasha, et al., Quantitative Assessment of Impedance Tomography for Temperature Measurements in Microwave Hyperthermia, *Clin. Phys. Physiol. Meas.*, 1998, Suppl. A, 49-53.

(Continued)

*Primary Examiner* — Michael Peffley
*Assistant Examiner* — Khadijeh Vahdat
(74) *Attorney, Agent, or Firm* — Zachary F. Madonna

(57) ABSTRACT

A tissue treatment selection device that has at least one treatment delivery member, a delivery setting circuit that is coupled to the treatment delivery member that is adapted to be deployed into tissue to deliver therapeutic energy to a target tissue zone, and the processing circuit is operable to set treatment parameters in the delivery setting circuit. The processing circuit is operable to transmit a test signal through the deployed treatment delivery member and to determine deployment status. The treatment selection device has a processing circuit adapted to send a message to a display device that indicates that the deployed treatment delivery member has been determined to be compensable and contains a suggested change in the treatment parameters. Also presented herein is a method of treating a tissue of a patient using the treatment delivery device.

14 Claims, 10 Drawing Sheets

(58) Field of Classification Search
CPC ...... A61B 2018/1425; A61B 2018/143; A61B 2018/0016; A61B 2018/00648; A61B 2018/00821; A61B 2018/00898; A61B 2018/1467; A61B 2018/00779; A61B 2018/124; A61B 2018/1475; A61B 2018/00654; A61B 2018/1823; A61B 2018/00755; A61B 2018/00773; A61B 2018/00922; A61B 2018/00928; A61B 2018/0094
USPC .............................................. 606/32–34, 41
See application file for complete search history.

(56) References Cited

U.S. PATENT DOCUMENTS

| | | | |
|---|---|---|---|
| 4,226,246 A | 10/1980 | Fragnet | |
| 4,262,672 A | 4/1981 | Kief | |
| 4,407,943 A | 10/1983 | Cole et al. | |
| 4,810,963 A | 3/1989 | Blake-Coleman et al. | |
| 4,907,601 A | 3/1990 | Frick | |
| 4,946,793 A | 8/1990 | Marshall, III | |
| 5,019,034 A | 5/1991 | Weaver et al. | |
| 5,052,391 A | 10/1991 | Silberstone et al. | |
| 5,058,605 A | 10/1991 | Slovak | |
| 5,098,843 A | 3/1992 | Calvin | |
| 5,134,070 A | 7/1992 | Casnig | |
| 5,173,158 A | 12/1992 | Schmukler | |
| 5,193,537 A | 3/1993 | Freeman | |
| 5,273,525 A | 12/1993 | Hofmann | |
| 5,283,194 A | 2/1994 | Schmukler | |
| 5,318,563 A | 6/1994 | Malis et al. | |
| 5,328,451 A | 7/1994 | Davis et al. | |
| 5,389,069 A | 2/1995 | Weaver | |
| 5,403,311 A | 4/1995 | Abele et al. | |
| 5,425,752 A | 6/1995 | Vu'Nguyen | |
| 5,439,440 A | 8/1995 | Hofmann | |
| 5,458,625 A | 10/1995 | Kendall | |
| 5,484,400 A * | 1/1996 | Edwards et al. | 604/22 |
| 5,533,999 A | 7/1996 | Hood et al. | |
| 5,536,240 A | 7/1996 | Edwards et al. | |
| 5,575,811 A | 11/1996 | Reid et al. | |
| 5,626,146 A | 5/1997 | Barber et al. | |
| 5,634,899 A | 6/1997 | Shapland et al. | |
| 5,674,267 A | 10/1997 | Mir et al. | |
| 5,702,359 A | 12/1997 | Hofmann | |
| 5,720,921 A | 2/1998 | Meserol | |
| 5,778,894 A | 7/1998 | Dorogi et al. | |
| 5,782,882 A | 7/1998 | Lerman et al. | |
| 5,800,378 A | 9/1998 | Edwards et al. | |
| 5,810,762 A | 9/1998 | Hofmann | |
| 5,836,905 A | 11/1998 | Lemelson et al. | |
| 5,843,026 A | 12/1998 | Edwards et al. | |
| 5,873,849 A | 2/1999 | Bernard | |
| 5,919,142 A | 7/1999 | Boone et al. | |
| 5,947,889 A | 9/1999 | Hehrlein | |
| 5,983,131 A | 11/1999 | Weaver et al. | |
| 5,991,697 A | 11/1999 | Nelson et al. | |
| 5,999,847 A | 12/1999 | Elstrom | |
| 6,009,347 A | 12/1999 | Hofmann | |
| 6,010,613 A | 1/2000 | Walters et al. | |
| 6,016,452 A | 1/2000 | Kasevich | |
| 6,041,252 A | 3/2000 | Walker et al. | |
| 6,055,453 A | 4/2000 | Hofmann et al. | |
| 6,068,650 A | 5/2000 | Nanda et al. | |
| 6,085,115 A | 7/2000 | Weaver et al. | |
| 6,090,106 A | 7/2000 | Goble et al. | |
| 6,102,885 A | 8/2000 | Bass | |
| 6,106,521 A | 8/2000 | Blewett et al. | |
| 6,109,270 A | 8/2000 | Mah et al. | |
| 6,122,599 A | 9/2000 | Mehta | |
| 6,132,419 A | 10/2000 | Hofmann | |
| 6,159,163 A | 12/2000 | Strauss et al. | |
| 6,208,893 B1 | 3/2001 | Hofmann | |
| 6,210,402 B1 | 4/2001 | Olsen et al. | |
| 6,212,433 B1 | 4/2001 | Behl | |
| 6,216,034 B1 | 4/2001 | Hofmann | |
| 6,219,577 B1 | 4/2001 | Brown et al. | |
| 6,241,702 B1 | 6/2001 | Lundquist et al. | |
| 6,261,831 B1 | 7/2001 | Agee | |
| 6,278,895 B1 | 8/2001 | Bernard | |
| 6,300,108 B1 | 10/2001 | Rubinsky | |
| 6,326,177 B1 | 12/2001 | Schoenbach et al. | |
| 6,347,247 B1 | 2/2002 | Dev et al. | |
| 6,349,233 B1 | 2/2002 | Adams | |
| 6,351,674 B2 | 2/2002 | Silverstone | |
| 6,387,671 B1 | 5/2002 | Rubinsky et al. | |
| 6,403,348 B1 | 6/2002 | Rubinsky et al. | |
| 6,470,211 B1 | 10/2002 | Ideker et al. | |
| 6,482,619 B1 | 11/2002 | Rubinsky et al. | |
| 6,493,592 B1 | 12/2002 | Leonard et al. | |
| 6,500,173 B2 | 12/2002 | Underwood et al. | |
| 6,508,815 B1 | 1/2003 | Strul et al. | |
| 6,526,320 B2 | 2/2003 | Mitchell | |
| 6,562,604 B2 | 5/2003 | Rubinsky et al. | |
| 6,607,529 B1 | 8/2003 | Jones et al. | |
| 6,611,706 B2 | 8/2003 | Avrahami et al. | |
| 6,613,211 B1 | 9/2003 | McCormick et al. | |
| 6,627,421 B1 | 9/2003 | Unger et al. | |
| 6,653,091 B1 | 11/2003 | Dunn et al. | |
| 6,669,691 B1 | 12/2003 | Taimisto | |
| 6,692,493 B2 | 2/2004 | McGovern et al. | |
| 6,697,669 B2 | 2/2004 | Dev et al. | |
| 6,697,670 B2 | 2/2004 | Chornenky et al. | |
| 6,702,808 B1 | 3/2004 | Kreindel | |
| 6,795,728 B2 | 9/2004 | Chornenky et al. | |
| 6,801,804 B2 | 10/2004 | Miller et al. | |
| 6,865,416 B2 | 3/2005 | Dev et al. | |
| 6,892,099 B2 | 5/2005 | Jaafar et al. | |
| 6,912,417 B1 | 6/2005 | Bernard et al. | |
| 6,927,049 B2 | 8/2005 | Rubinsky et al. | |
| 6,962,587 B2 | 11/2005 | Johnson et al. | |
| 6,972,014 B2 | 12/2005 | Eum et al. | |
| 6,994,706 B2 | 2/2006 | Chornenky et al. | |
| 7,053,063 B2 | 5/2006 | Rubinsky et al. | |
| 7,063,698 B2 | 6/2006 | Whayne et al. | |
| 7,130,697 B2 | 10/2006 | Chornenky et al. | |
| 7,211,083 B2 | 5/2007 | Chornenky et al. | |
| 7,267,676 B2 | 9/2007 | Chornenky et al. | |
| 2001/0044596 A1 | 11/2001 | Jaafar | |
| 2002/0010491 A1 | 1/2002 | Schoenbach | |
| 2002/0055731 A1 | 5/2002 | Atala et al. | |
| 2002/0072742 A1 * | 6/2002 | Schaefer et al. | 606/41 |
| 2002/0077676 A1 | 6/2002 | Schroeppel et al. | |
| 2002/0099323 A1 | 7/2002 | Dev et al. | |
| 2002/0138117 A1 | 9/2002 | Son | |
| 2002/0193831 A1 | 12/2002 | Smith, III | |
| 2003/0009110 A1 | 1/2003 | Tu et al. | |
| 2003/0060856 A1 | 3/2003 | Chornenky et al. | |
| 2003/0088189 A1 | 5/2003 | Tu et al. | |
| 2003/0130711 A1 | 7/2003 | Pearson et al. | |
| 2003/0170898 A1 | 9/2003 | Gundersen et al. | |
| 2003/0208200 A1 | 11/2003 | Palanker et al. | |
| 2003/0225360 A1 | 12/2003 | Eppstein et al. | |
| 2004/0019371 A1 | 1/2004 | Jaafar et al. | |
| 2004/0059389 A1 | 3/2004 | Chornenky et al. | |
| 2004/0146877 A1 | 7/2004 | Diss et al. | |
| 2004/0153057 A1 | 8/2004 | Davison | |
| 2004/0243107 A1 | 12/2004 | Macoviak | |
| 2004/0267189 A1 | 12/2004 | Mavor et al. | |
| 2005/0043726 A1 | 2/2005 | McHale et al. | |
| 2005/0049541 A1 | 3/2005 | Behar et al. | |
| 2005/0165393 A1 | 7/2005 | Eppstein | |
| 2005/0171522 A1 * | 8/2005 | Christopherson | 606/34 |
| 2005/0171523 A1 | 8/2005 | Rubinsky et al. | |
| 2005/0171574 A1 | 8/2005 | Rubinsky et al. | |
| 2005/0182462 A1 | 8/2005 | Chornenky et al. | |
| 2005/0261672 A1 | 11/2005 | Deem et al. | |
| 2005/0288730 A1 | 12/2005 | Deem et al. | |
| 2006/0015147 A1 | 1/2006 | Persson et al. | |
| 2006/0025760 A1 | 2/2006 | Podhajsky | |
| 2006/0074413 A1 * | 4/2006 | Behzadian | A61B 18/1477 606/41 |
| 2006/0079883 A1 | 4/2006 | Elmouelhi et al. | |

(56) References Cited

U.S. PATENT DOCUMENTS

| | | | |
|---|---|---|---|
| 2006/0121610 | A1 | 6/2006 | Rubinsky et al. |
| 2006/0212078 | A1 | 9/2006 | Demarais et al. |
| 2006/0217703 | A1 | 9/2006 | Chornenky et al. |
| 2006/0264752 | A1 | 11/2006 | Rubinsky et al. |
| 2007/0043345 | A1 | 2/2007 | Davalos et al. |
| 2007/0118069 | A1 | 5/2007 | Persson et al. |
| 2007/0118184 | A1 | 5/2007 | Danek et al. |
| 2008/0052786 | A1 | 2/2008 | Lin et al. |
| 2008/0125772 | A1* | 5/2008 | Stone et al. .................. 606/41 |
| 2008/0140064 | A1* | 6/2008 | Vegesna ...................... 606/34 |

FOREIGN PATENT DOCUMENTS

| | | |
|---|---|---|
| EP | 0378132 | 7/1990 |
| EP | 0935482 | 5/2005 |
| KR | 100505823 B1 | 8/2005 |
| WO | 9639531 | 12/1996 |
| WO | 0020554 | 4/2000 |
| WO | 0107583 | 2/2001 |
| WO | 0107584 | 2/2001 |
| WO | 0107585 | 2/2001 |
| WO | 0181533 | 11/2001 |
| WO | 2004037341 | 5/2004 |

OTHER PUBLICATIONS

Andreason, Electroporation as a Technique for the Transfer of Macromolecules into Mammalian Cell Lines, *J. Tiss. Cult. Meth.*, 15:56-62, 1993.

Baker, et al., Calcium-Dependent Exocytosis in Bovine Adrenal Medullary Cells with Leaky Plasma Membranes, *Nature*, vol. 276, pp. 620-622, 1978.

Barber, Electrical Impedance Tomography Applied Potential Tomography, Advances in Biomedical Engineering, Beneken and Thevenin, eds., IOS Press, 1993.

Beebe, S.J., et al., Nanosecond pulsed electric field (nsPEF) effects on cells and tissues: apoptosis induction and tumor growth inhibition. PPPS-2001 Pulsed Power Plasma Science 2001, 28$^{th}$ IEEE International Conference on Plasma Science and 13$^{th}$ IEEE International Pulsed Power Conference, Digest of Technical Papers (Cat. No. 01CH37251). IEEE, Part vol. 1, 2001, pp. 211-215, vol. I, Piscataway, NJ, USA.

Blad, et al., Impedance Spectra of Tumour Tissue in Comparison with Normal Tissue; a Possible Clinical Application for Electrical Impedance Tomography, *Physiol. Meas.* 17 (1996) A105-A115.

Bown, S.G., Phototherapy of tumors. *World J. Surgery*, 1983. 7: p. 700-9.

BPH Management Strategies: Improving Patient Satisfaction, *Urology Times*, May 2001, vol. 29, Supplement 1.

Brown, et al., Blood Flow Imaging Using Electrical Impedance Tomography, *Clin. Phys. Physiol. Meas.*, 1992, vol. 13, Suppl. A, 175-179.

Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.

Coates, C.W.,et al., "The Electrical Discharge of the Electric Eel, Electrophorous Electricus," Zoologica, 1937, 22(1), pp. 1-32.

Cook, et al., ACT3: A High-Speed, High-Precision Electrical Impedance Tomograph, *IEEE Transactions on Biomedical Engineering*, vol. 41, No. 8, Aug. 1994.

Cowley, Good News for Boomers, *Newsweek*, Dec. 30, 1996/Jan. 6, 1997.

Cox, et al., Surgical Treatment of Atrial Fibrillation: A Review, *Europace* (2004) 5, S20-S-29.

Crowley, Electrical Breakdown of Biomolecular Lipid Membranes as an Electromechanical Instability, *Biophysical Journal*, vol. 13, pp. 711-724, 1973.

Davalos, et al., Tissue Ablation with Irreversible Electroporation, *Annals of Biomedical Engineering*, vol. 33, No. 2, Feb. 2005.

Davalos, et al ., Theoretical Analysis of the Thermal Effects During In Vivo Tissue Electroporation, Bioelectrochemistry, vol. 61, pp. 99-107, 2003.

Davalos, et al., A Feasibility Study for Electrical Impedance Tomography as a Means to Monitor T issue Electroporation for Molecular Medicine, *IEEE Transactions on Biomedical Engineering*, vol. 49, No. 4, Apr. 2002.

Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.

Dean, Nonviral Gene Transfer to Skeletal, Smooth, and Cardiac Muscle in Living Animals, *Am J. Physiol Cell Physiol* 289: 233-245, 2005.

Dev, et al., Sustained Local Delivery of Heparin to the Rabbit Arterial Wall with an Electroporation Catheter, *Catheterization and Cardiovascular Diagnosis*, Nov. 1998, vol. 45, No. 3, pp. 337-343.

Dev, et al., Medical Applications of Electroporation, *IEEE Transactions of Plasma Science*, vol. 28, No. 1, pp. 206-223, Feb. 2000.

Duraiswami, et al., Boundary Element Techniques for Efficient 2-D and 3-D Electrical Impedance Tomography, *Chemical Engineering Science*, vol. 52, No. 13, pp. 2185-2196, 1997.

Duraiswami, et al., Efficient 2D and 3D Electrical Impedance Tomography Using Dual Reciprocity Boundary Element Techniques, *Engineering Analysis with Boundary Elements* 22, (1998) 13-31.

Duraiswami, et al., Solution of Electrical Impedance Tomography Equations Using Boundary Element Methods, *Boundary Element Technology* XII, 1997, pp. 226-237.

Edd, J., et al., In-Vivo Results of a New Focal Tissue Ablation Technique: Irreversible Electroporaton, *IEEE Trans. Biomed. Eng.* 53 (2006) p. 1409-1415.

Erez, et al., Controlled Destruction and Temperature Distributions in Biological Tissues Subjected to Monoactive Electrocoagulation, *Transactions of the ASME: Journal of Mechanical Design*, vol. 102, Feb. 1980.

Foster, R.S., et al., High-intensity focused ultrasound in the treatment of prostatic disease. *Eur. Urol.*, 1993. 23: 44-7).

Fox, et al., Sampling Conductivity Images via MCMC, Mathematics Department, Auckland University, New Zealand, May 1997.

Gauger, et al., A Study of Dielectric Membrane Breakdown in the Fucus Egg, *J. Membrane Biol.*, vol. 48, No. 3, pp. 249-264, 1979.

Gehl, et al., In Vivo Electroporation of Skeletal Muscle: Threshold, Efficacy and Relation to Electric Field Distribution, *Biochimica et Biphysica Acta* 1428, 1999, pp. 233-240.

Gençer, et al., Electrical Impedance Tomography: Induced-Current Imaging Achieved with a Multiple Coil System, *IEEE Transactions on Biomedical Engineering*, vol. 43, No. 2, Feb. 1996.

Gilbert, et al., Novel Electrode Designs for Electrochemotherapy, *Biochimica et Biophysica Acta* 1334, 1997, pp. 9-14.

Gilbert, et al., The Use of Ultrasound Imaging for Monitoring Cryosurgery, Proceedings 6$^{th}$ Annual Conference, IEEE Engineering in Medicine and Biology, 107-111, 1984.

Glidewell, et al., The Use of Magnetic Resonance Imaging Data and the Inclusion of Anisotropic Regions in Electrical Impedance Tomography, *Biomed, Sci. Instrum.* 1993; 29: 251-7.

Gothelf, et al., Electrochemotherapy: Results of Cancer Treatment Using Enhanced Delivery of Bleomycin by Electroporation, *Cancer Treatment Reviews* 2003: 29: 371-387.

Griffiths, et al., A Dual-Frequency Electrical Impedence Tomography System, *Phys. Med. Biol.*, 1989, vol. 34, No. 10, pp. 1465-1476.

Griffiths, The Importance of Phase Measurement in Electrical Impedance Tomography, *Phys. Med. Biol.*, 1987, vol. 32, No. 11, pp. 1435-1444.

Griffiths, Tissue Spectroscopy with Electrical Impedance Tomography: Computer Simulations, *IEEE Transactions on Biomedical Engineering*, vol. 42, No. 9, Sep. 1995.

Gumerov, et al., The Dipole Approximation Method and Its Coupling with the Regular Boundary Element Method for Efficient Electrical Impedance Tomography, *Boundary Element Technology* XIII, 1999.

(56) References Cited

OTHER PUBLICATIONS

Hapala, Breaking the Barrier: Methods for Reversible Permeabilization of Cellular Membranes, *Critical Reviews in Biotechnology*, 17(2): 105-122, 1997.
Heller, et al., Clinical Applications of Electrochemotherapy, *Advanced Drug Delivery Reviews*, vol. 35, pp. 119-129, 1999.
Ho, et al., Electroporation of Cell Membranes: A Review, *Critical Reviews in Biotechnology*, 16(4): 349-362, 1996.
Holder, et al., Assessment and Calibration of a Low-Frequency System for Electrical Impedance Tomography (EIT), Optimized for Use in Imaging Brain Function in Ambulant Human Subjects, *Annals of the New York Academy of Science*, vol. 873, Issue 1, Electrical BI, pp. 512-519, 1999.
Huang, et al., Micro-Electroporation: Improving the Efficiency and Understanding of Electrical Permeabilization of Cells, *Biomedical Microdevices*, vol. 2, pp. 145-150, 1999.
Hughes, et al., An Analysis of Studies Comparing Electrical Impedance Tomography with X-Ray Videofluoroscopy in the Assessment of Swallowing, *Physiol. Meas.* 15, 1994, pp. A199-A209.
Issa, et al., The TUNA Procedure for BPH: Review of the Technology: The TUNA Procedure for BPH: Basic Procedure and Clinical Results, Reprinted from *Infections in Urology*, Jul./Aug. 1998 and Sep./Oct. 1998.
Ivanuša, et al., MRI Macromolecular Contrast Agents as Indicators of Changed Tumor Blood Flow, *Radiol. Oncol.* 2001; 35(2): 139-47.
Jaroszeski, et al., In Vivo Gene Delivery by Electroporation, *Advanced Drug Delivery Review*, vol. 35, pp. 131-137, 1999.
Kinosita, et al., Hemolysis of Human Erythrocytes by a Transient Electric Field, *Proc. Natl. Acad. Sci. USA*, vol. 74, No. 5, pp. 1923-1927, 1977.
Liu, et al., Measurement of Pharyngeal Transit Time by Electrical Impedance Tomography, *Clin. Phys. Physiol. Meas.*, 1992, vol. 13, Suppl. A, pp. 197-200.
Lundqvist, et al., Altering the Biochemical State of Individual Cultured Cells and Organelles with Ultramicroelectrodes, *Proc. Natl. Acad. Sci. USA*, vol. 95, pp. 10356-10360, Sep. 1998.
Lurquin, Gene Transfer by Electroporation, *Molecular Biotechnology*, vol. 7, 1997.
Lynn, et al., A New Method for the Generation and Use of Focused Ultrasound in Experimental Biology, *The Journal of General Physiology*, vol. 26, 179-193, 1942.
Miklavčič, et al., A Validated Model of an in Vivo Electric Field Distribution in Tissues for Electrochemotherapy and for DNA Electrotransfer for Gene Therapy, *Biochimica et Biophysica Acta* 1523 (2000), pp. 73-83.
Miklavčič, et al., The Importance of Electric Field Distribution for Effective in Vivo Electroporation of Tissues, *Biophysical Journal*, vol. 74, May 1998, pp. 2152-2158.
Miller, L., et al., Cancer cells ablation with irreversible electroporation, *Technology in Cancer Research and Treatment* 4 (2005) 699-706.
Mir, Therapeutic Perspectives of In Vivo Cell Electropermeabilization, *Bioelectrochemistry*, vol. 53, pp. 1-10, 2000.
Mir, L.M., et al., Electric Pulse-Mediated Gene Delivery to Various Animal Tissues, in Advances in Genetics, Academic Press, 2005, p. 83-114.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Mir, et al., Effective Treatment of Cutaneous and Subcutaneous Malignant Tumours by Electrochemotherapy, *British Journal of Cancer*, vol. 77, No. 12, pp. 2336-2342, 1998.
Mir, et al., Electrochemotherapy Potentiation of Antitumour Effect of Bleomycin by Local Electric Pulses, *European Journal of Cancer*, vol. 27, No. 1, pp. 68-72, 1991.
Mir, et al., Electrochemotherapy, a Novel Antitumor Treatment: First Clinical Trial, *C.R. Acad. Sci. Paris*, Ser. III, vol. 313, pp. 613-618, 1991.

Narayan, et al., Establishment and Characterization of a Human Primary Prostatic Adenocarcinoma Cell Line (ND-1), *The Journal of Urology*, vol. 148, 1600-1604, Nov. 1992.
Naslund, Michael J., Transurethral Needle Ablation of the Prostate, *Urology*, vol. 50, No. 2, Aug. 1997.
Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.
Neumann, et al., Gene Transfer into Mouse Lyoma Cells by Electroporation in High Electric Fields, *J. Embo.*, vol. 1, No. 7, pp. 841-845, 1982.
Neumann, et al., Permeability Changes Induced by Electric Impulses in Vesicular Membranes, *J. Membrane Biol.*, vol. 10, pp. 279-290, 1972.
Okino, et al., Effects of High-Voltage Electrical Impulse and an Anticancer Drug on In Vivo Growing Tumors, Japanese Journal of Cancer Research, vol. 78, pp. 1319-1321, 1987.
Onik, et al., Sonographic Monitoring of Hepatic Cryosurgery in an Experimental Animal Model, *AJR American J. of Roentgenology*, vol. 144, pp. 1043-1047, May 1985.
Onik, et al., Ultrasonic Characteristics of Frozen Liver, *Cryobiology*, vol. 21, pp. 321-328, 1984.
Organ, L.W., Electrophysiological principles of radiofrequency lesion making, *Apply. Neurophysiol.*, 1976. 39: p. 69-76.
Piñero, et al., Apoptotic and Necrotic Cell Death Are Both Induced by Electroporation in HL60 Human Promyeloid Leukaemia Cells, *Apoptosis*, vol. 2, No. 3, 330-336, Aug. 1997.
Precision Office TUNA System, When Patient Satisfaction is Your Goal.
Rols, M.P., et al., Highly Efficient Transfection of Mammalian Cells by Electric Field Pulses: Application to Large Volumes of Cell Culture by Using a Flow System, *Eur. J. Biochem.* 1992, 206, pp. 115-121.
Rubinsky, B., ed, Cryosurgery. *Annu Rev. Biomed.* Eng. vol. 2 2000. 157-187.
Schmukler, Impedance Spectroscopy of Biological Cells, downloaded from IEEE Xplore website.
Sersa, et al., Reduced Blood Flow and Oxygenation in SA-1 Tumours after Electrochemotherapy with Cisplatin, *British Journal of Cancer*, 87, 1047-1054, 2002.
Sersa, et al., Tumour Blood Flow Modifying Effects of Electrochemotherapy: a Potential Vascular Targeted Mechanism, *Radiol. Oncol.*, 37(1): 43-8, 2003.
Sharma, et al., Poloxamer 188 Decreases Susceptibility of Artificial Lipid Membranes to Electroporation, *Biophysical Journal*, vol. 71, No. 6, pp. 3229-3241, Dec. 1996.
Shiina, S., et al, Percutaneous ethanol injection therapy for hepatocellular carcinoma: results in 146 patients. *AJR*, 1993, 160: p. 1023-8.
Thompson, et al., To determine whether the temperature of 2% lignocaine gel affects the initial discomfort which may be associated with its instillation into the male urethra, *BJU International* (1999), 84, 1035-1037.
TUNA—Suggested Local Anesthesia Guidelines.
Vidamed, Inc., Transurethral Needle Ablation (TUNA): Highlights from Worldwide Clinical Studies, Vidamed's Office TUNA System.
Weaver, Electroporation: A General Phenomenon for Manipulating Cells and Tissues, *Journal of Cellular Biochemistry*, 51: 426-435, 1993.
Weaver, et al., Theory of Electroporation: A Review, *Bioelectrochemistry and Bioenergetics*, vol. 41, pp. 136-160, 1996.
Zimmermann, et al., Dielectric Breakdown of Cell Membranes, *Biophysical Journal*, vol. 14, No. 11, pp. 881-899, 1974.
Zlotta, et al., Possible Mechanisms of Action of Transurethral Needle Ablation of the Prostate on Benign Prostatic Hyperplasia Symptoms: a Neurohistochemical Study, Reprinted from *Journal of Urology*, vol. 157, No. 3, Mar. 1997, pp. 894-899.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.

(56) References Cited

OTHER PUBLICATIONS

International search report in PCT/US09/48270 dated Feb. 11, 2010.
English translation of Abstract and Claim 1 of KR 100505823 B1.

* cited by examiner

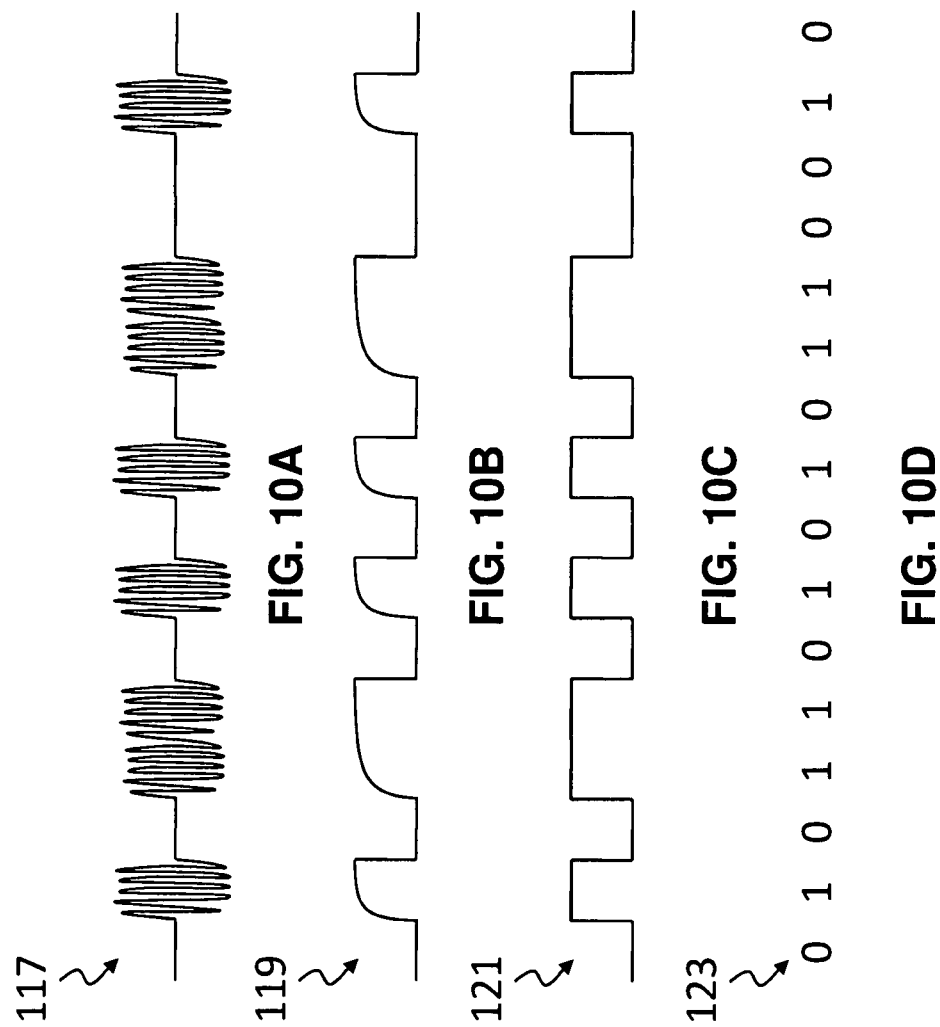

TREATMENT DEVICES AND METHODS

CROSS-REFERENCE TO RELATED APPLICATIONS

This application claims priority under 35 U.S.C. 119(e) to U.S. provisional application No. 61/074,853, filed Jun. 23, 2008, which is incorporated herein by reference.

FIELD OF THE INVENTION

The present application relates in general to devices that deliver one or more treatment modalities. More specifically, the application relates to devices and methods for using tissue treatment apparatuses that can include treatment delivery devices having multiple delivery members; and varying treatment deliveries through selection mechanisms in increasing efficiency, effectiveness, and safety levels.

BACKGROUND OF THE INVENTION

Current treatment devices utilizing two or more treatment delivery members are limited in usefulness due to the fact that during deployment or during use the spacing or resistance between each member can change, and lead to system disruption and failure. However, the current invention provides the advantages of detecting improper deployment as well as changes in environmental conditions and in certain cases, even actual and relative delivery member locations such that any irregularities can be corrected in real-time and if necessary, redeployment can be assured in an efficient manner and for patient benefit. This invention utilizes novel communication between a generator and a tissue treatment apparatus such that effective treatments can be carried out, and the tissue treatment apparatus does not shut down.

BRIEF SUMMARY

A treatment selection device is presented herein that has at least one treatment delivery member. The treatment selection device has a delivery setting circuit that is coupled to the treatment delivery member. The treatment delivery member is adapted to be deployed into the tissue to deliver therapeutic energy to a target tissue zone. The treatment selection device also has a processing circuit that is operable to set treatment parameters in the delivery setting circuit. The processing circuit is further operable to transmit a test signal through the deployed treatment delivery member and to determine whether a deployment status of the deployed treatment delivery member is compensable by a change in the treatment parameters without withdrawing the deployed treatment delivery member. The treatment selection device has a processing circuit that is adapted to send a message to a display device that indicates that the deployed treatment delivery member has been determined to be compensable and contains a suggested change in the treatment parameters.

Also presented herein is a method of treating a tissue of a patient using a treatment delivery device having at least one treatment delivery member. The method involves piercing a tissue with the treatment delivery member so as to deploy the treatment delivery member, applying a test signal through the deployed treatment delivery member, and determining, based on the test signal, whether a deployment status of the deployed treatment delivery member is compensable by a change in the treatment parameters without withdrawing the deployed treatment delivery member.

BRIEF DESCRIPTION OF THE DRAWINGS

FIGS. 10A-10D show waveforms, respectively, for a voltage level (such as for radiofrequency (RF)), a detected signal, and data bit to a controller, with FIG. 10D indicating correlating data in binary form.

DETAILED DESCRIPTION

Figure 1:
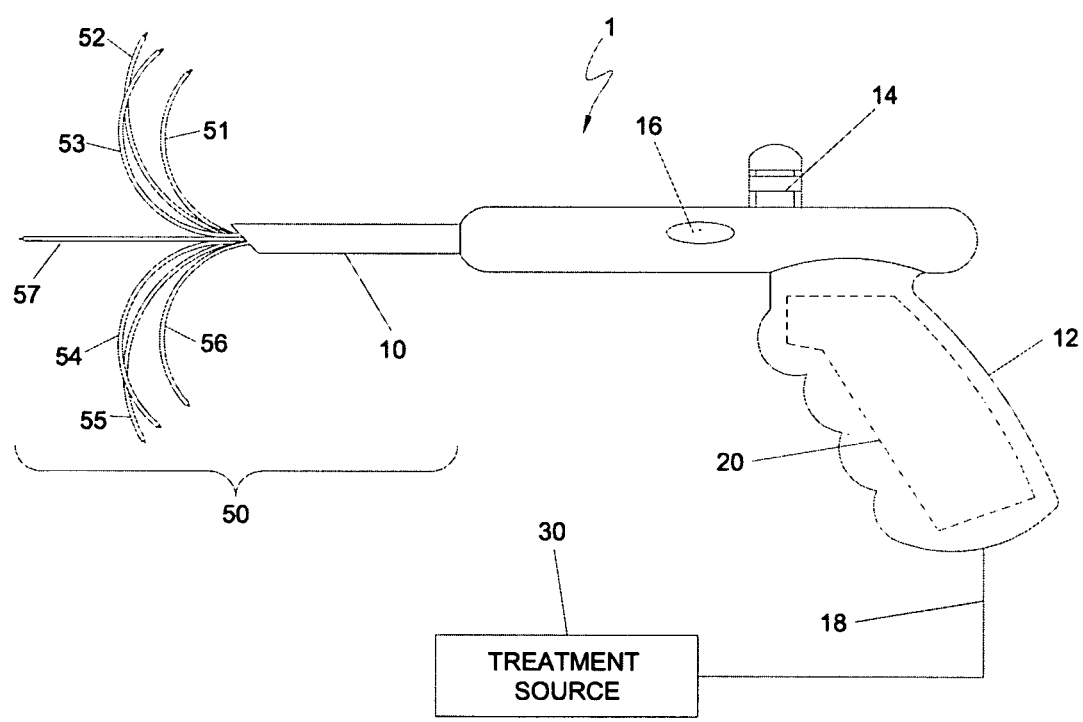
FIG. 1 is a partial elevational view of a tissue treatment apparatus according to the present application.

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a locking member" can include two or more such locking members unless the context indicates otherwise.

As used herein, the terms "optional" or "optionally" mean that the subsequently described event or circumstance may or may not occur, and that the description includes instances where said event or circumstance occurs and instances where it does not. The term "proximal" means closest to a practitioner, and the term "distal" means most distant from a practitioner.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Thus, for example, the reference to a microparticle is a reference to one such microparticle or a plurality of such microparticles, including equivalents thereof known to one skilled in the art. Also, as used herein and in the claims, the terms "at least one" and "one or more" have the same meaning and include one, two, three or more. The following terms, unless otherwise indicated, shall be understood to have the following meanings when used in the context of the present disclosure.

Other than in the operating examples, or unless otherwise expressly specified, all of the numerical ranges, amounts, values and percentages such as those for quantities of materials durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values can be used.

"Formed from" and "formed of" denote open claim language. As such, it is intended that a member "formed from" or "formed of" a list of recited components as well as materials be a member comprising at least these recited components as well as materials, and can further include other non-recited components as well as materials.

Examples provided herein, including those following "such as" and "e.g.," are considered as illustrative only of various aspects and features of the present disclosure and embodiments thereof, without limiting the scope of any of the referenced terms or phrases either within the context or outside the context of such descriptions. Any suitable equivalents, alternatives, and modifications thereof (including materials, substances, constructions, compositions, formulations, means, methods, conditions, etc.) known as well as available to one skilled in the art can be used or carried out in place of or in combination with those disclosed herein, and are considered to fall within the scope of the present disclosure. Throughout the present disclosure in its entirety, any and all of the one, two, or more features and aspects disclosed herein, explicitly or implicitly, following terms "example", "examples", "such as", "e.g.", and the likes thereof can be practiced in any combinations of two, three, or more thereof (including their equivalents, alternatives, and modifications), whenever and wherever appropriate as understood by one of ordinary skill in the art. Some of these examples are themselves sufficient for practice singly (including their equivalents, alternatives, and modifications) without being combined with any other features, as understood by one of ordinary skill in the art. Therefore, specific details disclosed herein are not to be interpreted as limiting, but merely as a basis for the claims and as a representative basis for teaching one skilled in the art to variously employ aspects and features of the present disclosure in virtually any appropriate manner.

Conventional devices and designs for tissue treatment devices, including those for RF tissue ablation, have a non-changeable positive polarity for all deployable and non-deployable RF electrodes, and a non-changeable negative polarity for all ground pads (i.e., body-surface return electrodes). Such designs limit the amount of power that can be supplied through the RF electrode and the performance of such conventional devices. Prior commercialization efforts of bipolar RF devices have failed in part because such devices have a single RF pole coupled directly to multiple RF electrodes. When one or more of the RF electrodes is mis-deployed, an asymmetrical electrical field is created. As a result, a tissue treatment device can short out and become unusable. The control and adjustment features of the present application are lacking in conventional devices and designs for treatment delivery (e.g., radiofrequency ablation), which render them incapable of detecting or compensating for mis-deployment of treatment delivery members or changing treatment delivery parameters in real time. Physicians using such conventional devices can unknowingly deliver ineffective treatment to a patient.

Various examples of treatment selection devices are disclosed in the present application. The treatment selection devices can include a processor (or processors) that is electrically coupled to multiple selection mechanisms and configured for changing at least one of the selection mechanisms from a first setting to a second setting. The processor can include a microprocessor or a microcontroller. The selection mechanisms can include relays, transistors, thyristors, semiconductor controlled rectifiers, other switches, and combinations of two or more thereof.

In one aspect, the treatment selection device disclosed herein can be coupled to at least one mechanism that is capable of data storage. The at least one data storage mechanism can be used for recording the first and second settings, as well as a sequence of one or more setting changes. The data storage mechanisms can include a non-volatile computer memory, such as read-only memory and flash memory. When electrically coupled to a treatment source, the treatment selection device, the processor therein, as well as the data storage mechanisms therein can communicate with the treatment source using a one-way or two-way method.

The treatment selection device can further include mechanisms capable of energy storage. The energy storage mechanisms can be used for powering the processor as well as for powering the multiple selection mechanisms. The energy storage mechanisms can include capacitors and batteries. In certain examples, the energy storage mechanisms (also called a power storage device) can be configured to be energized by a portion of a treatment energy output or a non-treatment energy output, which can be provided by a treatment source or an auxiliary energy source. The output of the energy storage mechanisms can be a direct current, which can have a voltage less than that of the treatment energy.

The treatment selection device can be electrically coupled to a single treatment source or to multiple treatment sources. A treatment source can be a device such as a generator that is capable of converting one form of energy to another or otherwise providing energy to the energy delivery device for treatment, therapy or tissue ablation as energy moves from the elongated portion of the energy delivery device to the treatment delivery members and ultimately to tissue. The treatment selection device can be electrically coupled to a single treatment delivery device that includes multiple treatment delivery members, or to multiple treatment delivery devices, each including the same or different number of treatment delivery member or members. Each treatment delivery member can be electrically coupled to one or more selection mechanisms in the treatment selection device. Each treatment delivery member can have a distally positioned electrically conductive outer surface, while the remainder of the treatment delivery member and its electrical coupling to the treatment selection device can be insulated.

The change in the selection device from the first setting to the second setting can effect a change at the treatment delivery device from a first setting of treatment delivery to a second setting of treatment delivery. The change from the first setting to the second setting can be programmed to take place automatically without user intervention, provided that certain predetermined conditions are met (such as detection of mis-deployment of the treatment delivery members, or activation or termination of treatment procedure). Alternatively, the change from the first setting to the second setting can be effected by user intervention, either manually (such as by flipping a switch, pushing a button) or through allowed reprogramming of an algorithm. The difference between the first and second settings of treatment delivery can include different combinations of the treatment delivery members through which the treatment is delivered.

The treatment selection device can further include a sensing mechanism for sensing the delivery of treatment as well as for sensing the termination of treatment from the treatment source to the treatment delivery device. The sensing mechanism can include a sensing circuit. Algorithms for distributing treatment among the various treatment delivery members can involve sequential grouping thereof. Treatment can be delivered through adjacent pairs of treatment delivery members in bipolar mode consecutively or simultaneously.

Alternatively, treatment can be delivered through non-adjacent pairs of treatment delivery members in bipolar mode consecutively or simultaneously. Optionally, the device can be set up to prevent certain patterns or certain repeated sequences of treatment delivery members for patient safety or effectiveness. Treatment can also be delivered through groups of multiple treatment delivery members paired with other multiple treatment delivery members in bipolar mode. Treatment can further be delivered through a single selected treatment delivery member, or multiple selected delivery members, paired with multiple treatment delivery members that are substantially equivalently positioned with respect to three selected treatment delivery members. Treatment can further be delivered through one, two or more, or all of the treatment delivery members in monopolar mode to ensure that complete treatment is delivered to the target tissue. Without being limited thereto, the devices disclosed herein can provide complete and individualized treatment delivery controls to individual treatment delivery members independent of other such members. Such controls include treatment on/off switching; treatment parameter assignment (e.g., electrical polarity, output power level, duration of treatment), and selection of different groups of treatment delivery members for treatment delivery at any time point, but not limited thereto. With the devices, designs, and algorithms disclosed herein, tissue treatment rate and efficiency can be significantly improved.

Alternating the treatment delivery pattern across the multiple treatment delivery members (e.g., changing the number of members actively delivering treatment and their polarities) in a predefined algorithm can optimize the tissue treatment and can circulate more treatment energy through the treatment delivery members. Referring now to FIG. 1, a tissue treatment apparatus 1 is illustrated therein, which can include a handle 12 that is coupled to a treatment delivery device 50 that includes multiple treatment delivery members 51-57 (e.g., forming an electrode flower) and the elongated member 10 (e.g., probe). Handle 12 of the tissue treatment apparatus can be coupled to a treatment source 30 (e.g., generator) that includes multiple treatment delivery members 51-57 (e.g., forming an electrode flower) and an elongated member 10 (e.g., probe). Handle 12 of the tissue treatment apparatus can be coupled to a treatment source 30 (e.g., generator), and in one embodiment this coupling can be via a cabling 18.

The tissue treatment apparatus can further include a treatment selection device 20, which can be configured for coupling to treatment source 30 through cabling 18 or a separate coupling method. Treatment selection device 20 can be incorporated partially or fully into handle 12 as shown. Alternatively, treatment selection device 20 can be incorporated partially or fully in the connection between cabling 18 and handle 12, in the connection between cabling 18 and treatment source 30, along cabling 18. Treatment selection device 20 can also be located in a separable unit that is configured for coupling to handle 12 and for coupling to the treatment source 30. Handle 12 can further include a deployment mechanism 14 (e.g., slider) configured to expose at least a portion of treatment delivery members 51-57 partially or fully out of a distal portion of elongated member 10 (e.g., from a single opening or multiple openings at its distal and in certain embodiments through one or more side openings arranged annularly around as well as in certain cases longitudinally along member 10). Deployment mechanism 14 can also be configured to retract at least a portion of treatment delivery members 51-57 back into elongated member 10. Handle 12 can further include one or more actuating members 16 for enabling treatment delivery through treatment delivery members 51-57 or a portion thereof. One or more (or each) of treatment delivery members 51-57 can have a distally disposed treatment delivery outer surface (e.g., being electrically conductive), while the remainder of the treatment delivery member and its coupling (via, for example, conductor such as copper wire) to treatment selection device 20 can be isolated (e.g., electrically insulated) from other treatment delivery members and their coupling to treatment selection device 20. Any two adjacent treatment delivery members can have a minimum distance between their respective treatment delivery outer surfaces (i.e., two points on the respective two surfaces that are closest to each other) of 0.5 cm or greater, such as 1.5 cm or greater, or 2 cm or greater, or 2.5 cm or greater.

Treatment source 30 can be configured for providing one, two or more treatment modalities, such as electromagnetic (e.g., radiofrequency, microwave) energy, thermal energy modalities, nonthermal (e.g., electroporative), irreversible electroporation (and other nonthermal or thermal modalities), energy, mechanical (e.g., ultrasound) energy, fluidic materials and compositions, among others, to treatment delivery device 50. Treatment delivery device 50 can include two or more treatment delivery members that are deployable, and in certain cases, non-deployable, configured as described herein or as known to those skilled in the art. Examples of deployable treatment delivery members include members 51-57, which can be curved or linear, flexible or rigid, solid or hollow, with or without openings, or combinations of two or more thereof. Deployable treatment delivery members can be deployed independently, such as individually, or in groups of two or more thereof, or altogether simultaneously, or in predefined sequences, or combinations thereof. Examples of non-deployable treatment delivery members include one or more distal portions (e.g., segments, bands, strips, coils, spirals) of elongated member 10 (not shown).

In exemplary aspect, treatment source 30 can include a generator (e.g., a radiofrequency (RF) generator), capable of providing an electrical signal (e.g., thermal ablative RF energy) as a testing as well as in certain cases a sensing signal or a tissue treatment modality to treatment delivery device 50. Treatment delivery device 50 can include three or more (e.g., 4, 5, 6, 7 or more) deployable treatment delivery members, such as members 51-57. One or more (or each) of the treatment delivery members can include one or more lumens configured as fluid conduits as well as wiring conduits for sensors (e.g., thermal sensors such as thermocouples). Three or more of the treatment delivery members can be configured as electrodes (e.g., RF electrodes). Two or more of the treatment delivery members can be deployable with the same or different curvature. One or more of the treatment delivery members can be deployable substantially without curvature (e.g., linearly). Each of the treatment delivery members can independently include a tissue piercing tip that is closed or open.

Figure 2:
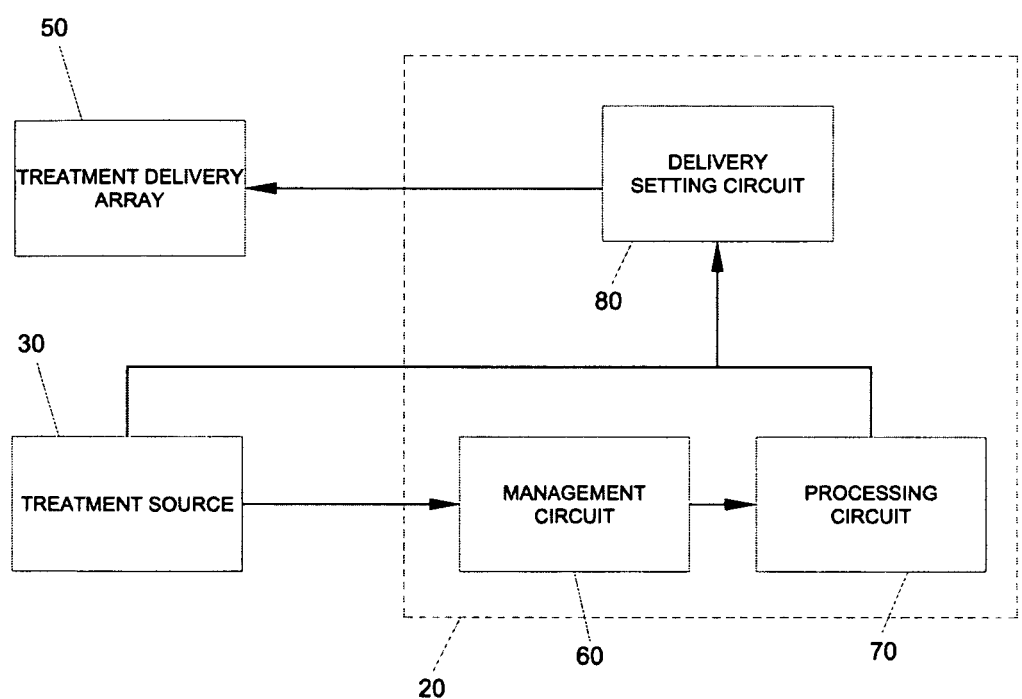
FIG. 2 is a generalized circuit diagram illustrating certain components of a tissue treatment apparatus according to the present application.

Referring now to FIG. 2, a diagrammatic illustration of a tissue treatment apparatus is shown. Treatment selection device 20 can include a management circuit 60, a processing circuit 70, and a delivery setting circuit 80. Management circuit 60 can include one or more sensing mechanisms (e.g., a sensing circuit) that actively or passively sense one or more changes in one or more treatment modalities provided from treatment source 30 to treatment delivery device 50. Management circuit 60 can use the one or more sensing mechanisms to control activation or initiation of processing circuit 70.

Management circuit 60 can further provide a stored energy to power processing circuit 70 as well as delivery setting circuit 80. Power storage device in management circuit 60 can include one or more capacitors as well as batteries. Management circuit 60 can further include one or more regulating methods to regulate power output to processing circuit 70 as well as delivery setting circuit 80.

Based on the sensed changes (e.g., testing, treatment, error) provided by treatment source 30 that is passed on from management circuit 60, processing circuit 70 can be activated or initiated, remain in the course of action (e.g., continue testing or treatment delivery), or carry out a set of instructions (e.g., to report testing results, to provide an error message, or to change the setting of delivery setting circuit 80), among other pre-determined options. Sensed changes in treatment provided by treatment source 30 can include changes between delivery on and delivery off, changes (e.g., increases or decreases) in strength (e.g., magnitude in energy level or flow rate), feedback signals resulting from physical, chemical, as well as performance data (e.g., temperature, impedance) gathered by sensors, but not limited thereto.

Delivery setting circuit 80 can include multiple selection mechanisms, such that each of the treatment delivery members in treatment delivery device 50 can be electrically coupled to one, two or more of the selection mechanisms in delivery setting circuit. As such, change of delivery setting circuit 80 from a first setting to a second setting can result in a change (e.g., begin, end, increase, decrease) of at least one treatment delivery member in treatment delivery device 50 in at least one aspect (such as power on or off status, polarity, amplitude or duration of treatment) of its treatment delivery from a first setting (e.g., treatment delivery enabled, positive polarity connection) to a second setting (e.g., treatment delivery disabled, negative polarity connection). Treatment delivery after the setting change can be in accordance with the second setting of delivery setting circuit 80 as well as the second treatment delivery setting of the at least one treatment delivery member of treatment delivery device 50.

In one example, management circuit 60 can sense that treatment is provided by treatment source 30 (i.e., delivery on), and initiate or activate processing circuit 70. Power storage device within management circuit 60 can be energized during the "delivery on" period. Processing circuit 70 can decide not to change the setting of delivery setting circuit 80, and treatment is delivered from treatment source 30 to treatment delivery device 50 through delivery setting circuit 80 at the existing setting of delivery setting circuit 80. In another example, management circuit 60 can sense that treatment from treatment source 30 is terminated (i.e., "delivery off"), and inform processing circuit 70 as such. Processing circuit 70 can decide to use the power in the power storage device to change delivery setting circuit 80 from a first setting to a second setting, such that at least one treatment delivery member of treatment delivery device 50 is changed from a first treatment delivery setting (e.g., treatment delivery enabled) to a second treatment delivery setting (e.g., treatment delivery disabled). When treatment from treatment source 30 is turned back on again, treatment delivery through the at least one treatment delivery member can, as a result of the change in setting within delivery setting circuit 80 during the "delivery off" period, be disabled.

Figure 3:
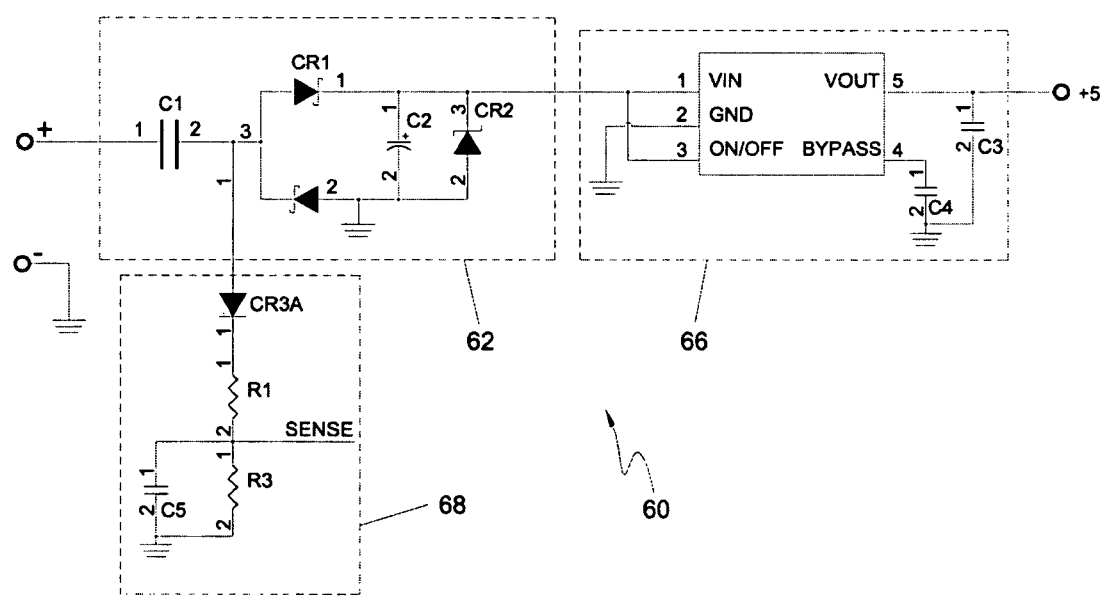
FIG. 3 is a diagram illustrating certain components of a management circuit.

Referring now to FIG. 3, an exemplary management circuit 60 is illustrated, the design of which is capable of accomplishing the sensing and power output functions disclosed herein. Management circuit 60 can include a power storage circuit 62.

Power storage circuit 62 can include one, two or more power storage device (e.g., capacitors, batteries), such as capacitors C1 and C2. Power storage circuit 62, as illustrated herein, can convert a portion of an incoming energy (e.g., alternating current, such as RF test or treatment energy, can be voltage modulated or current modulated) into direct current and store the power for later use. Specifically, incoming energy can charge capacitor C1, the output of which can be rectified by the remainder of power storage circuit 62 to charge capacitor C2. In one alternative, power storage circuit 62 can be configured to take incoming direct current and store the power for later use. In another alternative, power storage circuit 62 can include one or more batteries as power storage devices.

Management circuit 60 can run on a voltage lower than that required for treatment delivery device 50, such as 50V or less, or 10V or less, or 5V or less. Management circuit 60 can further include a regulating circuit 66, such that output of power storage circuit 62 can be properly regulated (e.g., stepping down from 10V to 5V) to be suitable for powering processing circuit 70 and delivery setting circuit 80 (shown in FIG. 2). Power storage devices in regulating circuit 66, such as capacitor C3, can also serve in part the function of power storage in management circuit 60.

Referring now to FIGS. 2 and 3, management circuit 60 can further include a sensing circuit 68 that is configured to initiate or activate processing circuit 70 when treatment delivery is deemed to be "on". For example, when treatment source 30 includes a generator, the generator can send out pulses (e.g., 0.1 second in duration and at 1 Hz, for testing as well as signaling stand-by mode) when in idle mode. It can take a certain amount of time (e.g., 1 second) for electrical energy (e.g., RF treatment energy) delivered from the generator to fully charge capacitor C2 in power storage circuit 62. As such, sensing circuit 68 can be configured to sense a continuous electrical energy (e.g., RF treatment energy) delivery of a predetermined period (e.g., 10 seconds or less, 5 seconds or less, 2 seconds or longer) before initiating or activating processing circuit 70. The predetermined period can be chosen to be sufficiently long (e.g., longer than generator pulse durations during testing as well as stand-by modes) to allow energy storage member(s), such as C1 as well as C2, to be fully charged. This way, processing circuit 70 can not be unintentionally initiated or activated when treatment delivery is not on.

Figure 4:
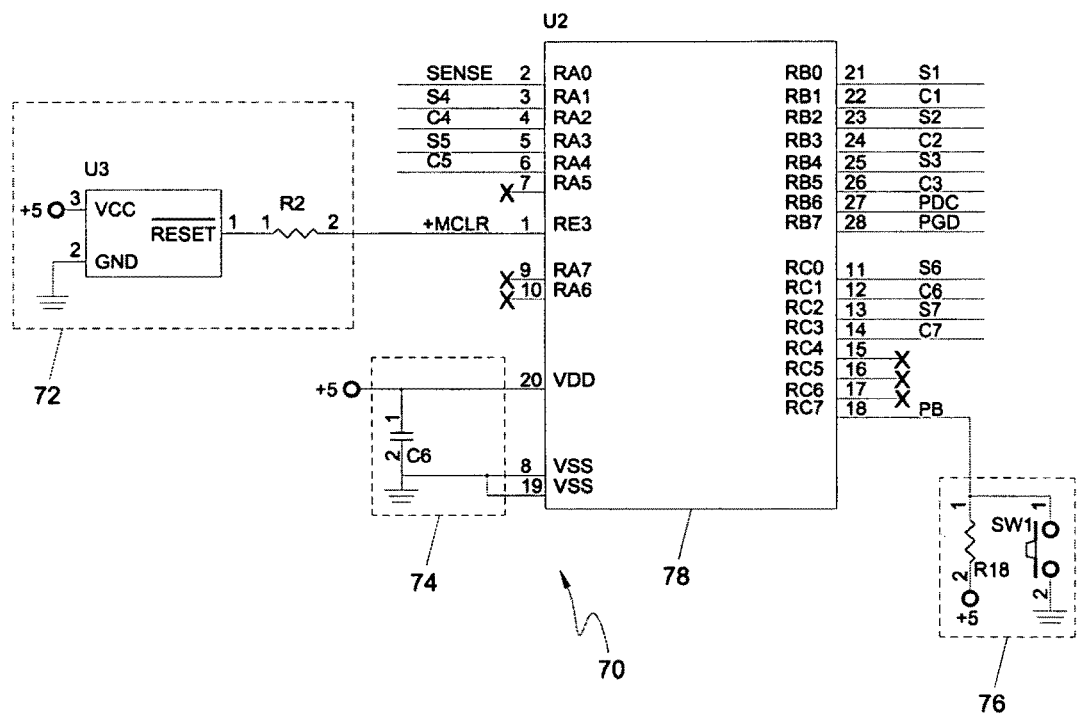
FIG. 4 is a diagram illustrating certain components of a processing circuit.

Referring now to FIG. 4, an exemplary processing circuit 70 is shown. Processing circuit 70 can include an integrated circuit 78, such as a microprocessor. Processing circuit 70 can further include non-volatile computer memory. The memory can be for storing pre-programmed delivery setting sequences as well as other data (e.g., commands, parameters, algorithms, software), as well as recording changes in delivery settings (e.g., treatment delivery on/off) and other events (e.g., error occurrences) as they occur during procedures. The memory can be physically one or more elements separate from the integrated circuit, or onboard the integrated circuit (e.g., as in a microcontroller).

Processing circuit 70 can further include a resetting circuit 72 to ensure integrated circuit 78 starts correctly when sensing circuit 68 (shown in FIG. 3) senses treatment delivery from treatment source 30 being on and initiates or activates integrated circuit 78. Processing circuit 70 can further include a by-pass filtering circuit 74 to filter power supply. Processing circuit 70 can further include a testing switch circuit 76 to reset the multiple selection mechanisms in delivery setting circuit 80 (FIG. 3) during use as well as testing of the apparatus.

Figure 5:
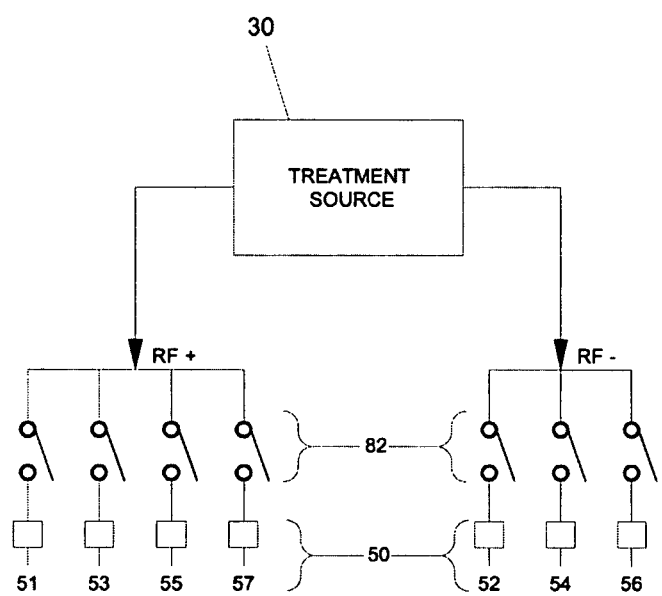
FIG. 5 is a diagram illustrating a configuration of multiple selection methods in coupling with multiple treatment delivery members.

Referring now to FIG. 5, a configuration is shown that includes multiple selection mechanisms in a selection mechanisms array 82 in coupling with multiple treatment delivery members in a treatment delivery device 50. Selection mechanisms array 82 can be included in delivery setting circuit 80, as shown in FIG. 2. Multiple selection mechanisms in selection mechanism array 82 can include any and all electronic switches, such as relays, transistors, thyristors (e.g., semiconductor-controlled rectifiers), and combinations of two or more thereof, but not limited thereto. Treatment can be delivered through different subsets (e.g., pairs, triplets, fours, fives, up to all) of treatment delivery members (e.g., members 51-57) in serial as well as in certain embodiments in parallel to prevent or reduce occurrence of rapid impedance rising of the neighboring tissue, reconfigure treatment delivery pattern to compensate for compensable mis-deployment of one or more treatment delivery members, increase treatment speed, increase treatment volume, enhance treatment uniformity and efficiency, reduce treatment duration, enhance treatment safety, as well as reduce treatment error.

Multiple selection mechanisms shown in FIG. 5 can be in one-to-one electric coupling with multiple treatment delivery members 51-57 in treatment delivery device 50. Each selection mechanism can be in one of two settings at any time: on or off (FIG. 5 shows an example "off" position). Electric coupling of each selection mechanism to treatment source 30 can be pre-determined in polarity. When a signal (e.g., treatment) provided by treatment source 30 is electrical (e.g., RF energy), each of treatment delivery members 51, 53, 55 and 57 can be in one of two settings at any time: positive electrical polarity (e.g., RF+) or "off", while each of treatment delivery members 52, 54, and 56 can be in one of two settings at any time: negative electrical polarity (e.g., RF−) or "off". In one example, an algorithm of treatment/testing delivery through different subsets of treatment delivery members is illustrated in Table 1 below. Treatment/testing can be delivered through adjacent pairs of treatment delivery members (e.g., groupings 1-6) in bipolar mode (which is significantly more efficient than monopolar mode) consecutively (as shown) or simultaneously (not shown). Alternatively, treatment/testing can be delivered through non-adjacent pairs of treatment delivery members (e.g., 51-53, 52-54, 53-55, 54-56, 55-51, 56-52) in bipolar mode consecutively or simultaneously.

Optionally, treatment/testing can not be delivered through any one of the treatment delivery members during two consecutive pairings of the treatment delivery members (e.g., to avoid overheating of the treatment delivery members during thermal treatment delivery). Treatment/testing can also be delivered through groups of multiple treatment delivery members paired with other multiple treatment delivery members (e.g., groupings 7-9), also in bipolar mode for high efficiency. Treatment/testing can further be delivered through a single selected treatment delivery member (e.g., grouping 10), or multiple selected delivery members (e.g., grouping 11), paired with multiple treatment delivery members that are substantially equivalently positioned with respect to the selected treatment delivery member, also in bipolar mode for high efficiency. Treatment/testing can further be delivered through one, two or more, or all of the treatment delivery members in monopolar mode (not shown) to ensure complete treatment/testing being delivered to the target tissue.

TABLE 1

| Groupings in algorithm | RF+ Members | RF− Members | Off Members |
|---|---|---|---|
| 1 | 51 | 52 | 53-57 |
| 2 | 53 | 54 | 51-52, 55-57 |
| 3 | 55 | 56 | 51-54, 57 |
| 4 | 53 | 52 | 51, 54-57 |
| 5 | 55 | 54 | 51-53, 56-57 |
| 6 | 51 | 56 | 52-55, 57 |
| 7 | 53, 55 | 52, 56 | 51, 54, 57 |
| 8 | 51, 53 | 54, 56 | 52, 55, 57 |
| 9 | 51, 55 | 52, 54 | 53, 56-57 |
| 10 | 57 | 52, 54, 56 | 51, 53, 55 |
| 11 | 51, 53, 55, 57 | 52, 54, 56 | |

Figure 6:
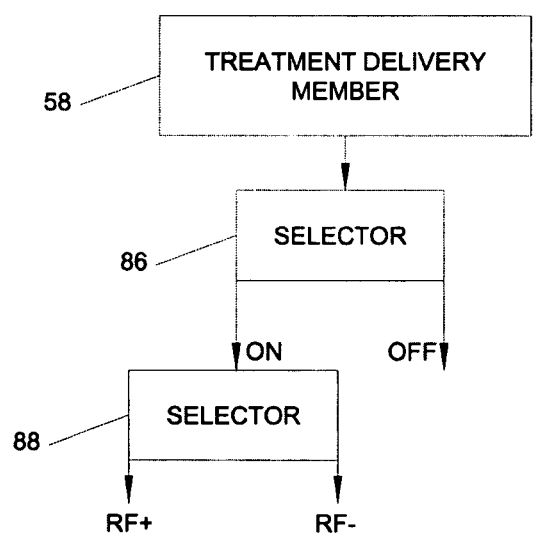
FIG. 6 is a diagram illustrating a configuration of two selection mechanisms in coupling with a treatment delivery member.
Figure 8:
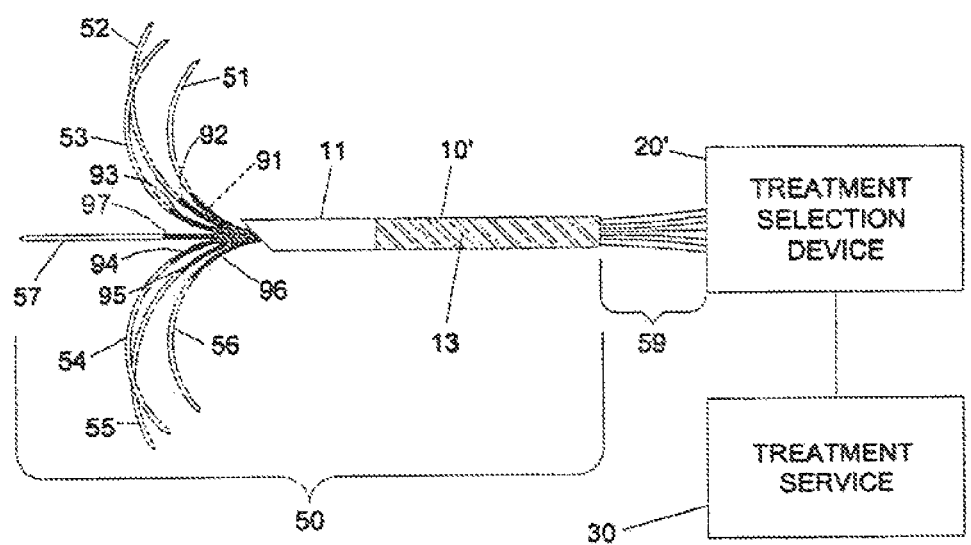
FIG. 8 is a diagram illustrating a tissue treatment apparatus including a treatment selection device, among other components, according to the present application.

In another example, a distal portion 11 of elongated member 10' (as shown in FIG. 8) can be configured as another treatment delivery member 58, illustrated in FIG. 6, with polarity and an activation state (such as negative electrical polarity), in addition to treatment delivery members 51-57. Another algorithm of treatment/testing delivery through different subsets of treatment delivery members in an embodiment where delivery member 58 is capable of activation is illustrated in Table 2 below.

TABLE 2

| Groupings in algorithm | RF+ Members | RF− Members | Off Members |
| --- | --- | --- | --- |
| 1 | 51 | 52 | 53-57 |
| 2 | 53 | 54 | 51-52, 55-57 |
| 3 | 55 | 56 | 51-54, 57 |
| 4 | 53 | 52 | 51, 54-57 |
| 5 | 55 | 54 | 51-53, 56-57 |
| 6 | 51 | 56 | 52-55, 57 |
| 7 | 53, 55 | 52, 56 | 51, 54, 57 |
| 8 | 51, 53 | 54, 56 | 52, 55, 57 |
| 9 | 51, 55 | 52, 54 | 53, 56-57 |

Referring now to FIG. 6, a configuration is shown that illustrates an example of using multiple selection mechanisms in branched configuration to independently provide any one treatment delivery member with more than two possible settings. Specifically, when treatment delivery member 58 is configured for delivering an electrical signal (e.g., RF energy), two selection mechanisms 86 and 88 can be coupled in a branched configuration to provide treatment delivery member 58 with one of three settings at any given time: positive or negative electrical polarities (e.g., RF+, RF−), or off.

Figure 7:
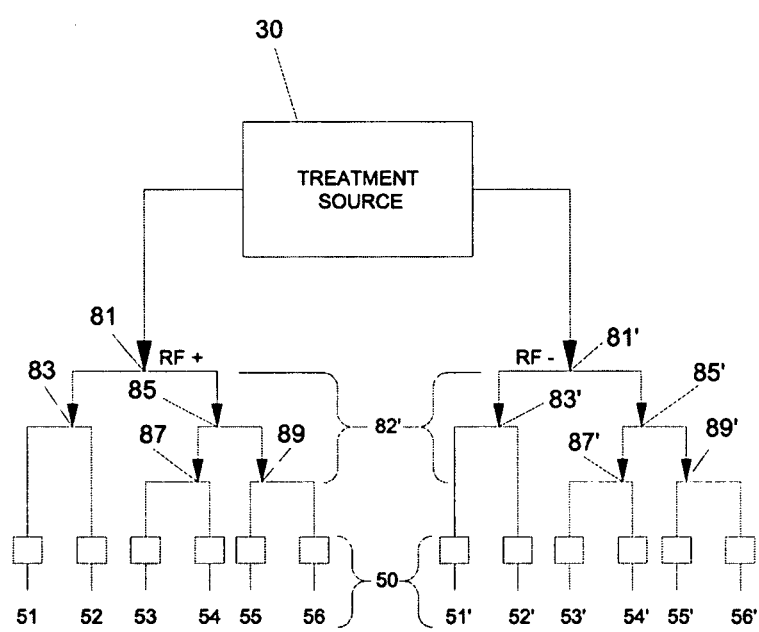
FIG. 7 is a diagram illustrating an alternate configuration of multiple selection mechanisms in coupling with multiple treatment delivery members.

Referring now to FIG. 7, a configuration is shown that illustrates an example of using multiple selection mechanisms in branched configuration to independently provide each of two or more treatment delivery members with more than two possible settings. Specifically, when treatment source 30 is configured to provide an electrical signal (such as RF energy), multiple selection mechanisms 81, 81', 83, 83', 85, 85', 87, 87', and 89 and 89' (of a selection mechanisms array 82') can be coupled in a branched configuration to provide each of treatment delivery members 51-57 with various settings. FIG. 7 shows 51-56 as an example embodiment, through the states including, but not limited to, an activation state, and polarity can also be conceivably changed for 57. In one exemplary aspect, in certain configurations, selection mechanism 81 can lead to an RF+ setting for treatment delivery members 51-57, while selection mechanism 81' can lead to an RF− setting for treatment delivery members 51'-56'. The additional selection mechanisms of mechanism array 82' (mechanisms 83, 83', 85, 85', 87, 87', and 89 and 89') are included to show that additional characteristics or settings of the treatment delivery members can be changed in the same way that the RF setting (positive or negative) was changed by 81 and 81'.

Referring now to FIG. 8, an alternative tissue treatment apparatus is illustrated, where treatment selection device 20 can be a handle, a device positioned along a cable, an electrical connector, or a stand-alone box (e.g., a set-top box) configured to be coupled with both treatment source 30 and the treatment delivery 50'. Elongated member 10' includes a distal portion 11 having an electrically conductive outer surface, which can be used for treatment delivery member 58 as described herein above and as also illustrated in FIG. 6. Distal portion 11 can be sharpened for piercing into or through at least soft tissues.

The remainder of elongated member 10' can be substantially isolated, such as being electrically insulated by insulation 13. In one aspect, insulation 13 can have an outer diameter greater than or equal to that of distal portion 11. Insulation 13 can be fixedly coupled to elongated member 10'. Alternatively, insulation 13 or a portion thereof (e.g., an outer insulation sleeve) can be movably coupled to elongated member 10', such as being able to rotate about as well as slide along elongated member 10'. Treatment delivery members 51-57 can each independently include a distal portion having an electrically conductive outer surface, and these distal portions can be sharpened for piercing into or through at least soft tissues. The remainders of treatment delivery members 51-57 can be substantially isolated, such as being electrically insulated by insulations 91-97, respectively. Insulations 91-97 can independently have an outer diameter greater than or equal to that of distal portions of treatment delivery members 51-57. Insulations 91-97 can be fixedly coupled to treatment delivery members 51-57, respectively.

Alternatively, insulations 91-97 or portions thereof (e.g., outer insulation sleeves) can be movably coupled to treatment delivery members 51-57, such as being able to rotate about as well as slide along treatment delivery members 51-57. Moveable insulations 91-97 or movable portions thereof can move independently of each other, in groups of two or more thereof, or be coupled together for simultaneous movement. Adjacent distal ends of insulations 91-97 and insulation 13 can have a distance (equivalent to minimum distance of adjacent conductive surfaces of treatment delivery members 51-57 and distal portion 11) of at least 1 cm, such as 1.5 cm or greater, or 2 cm or greater, or 2.5 cm or greater. This distance limitation can reduce or eliminate inadvertent electrical shorting when an electrical signal (e.g., RF energy) is applied between these adjacent conductive surfaces in a bipolar mode. For each of treatment delivery members 51-57, electrical insulation can extend from distal ends of insulations 91-97 continuously in the proximal direction throughout the entire portions within elongated member 10', and can include the separate conductors that electrically couple treatment delivery members 51-57 to treatment selection device 20', which are shown as insulated wires 59.

A separate conductor that electrically couples distal portion 11 (i.e., treatment delivery member 58) of elongated member 10' to treatment selection device 20' is also completely insulated and included in insulated wires 59. The complete electrical insulation of each electrically conductive outer surface from the others can allow completely independent and full control of each electrically conductive outer surface at any time before, during, or after testing as well as treatment delivery, and can make it possible for real time, in situ, reassignment of settings (e.g., on/off, negative/positive polarity) for any one of the treatment delivery members.

The treatment selection device 20' can be electrically coupled to a single treatment source 30 or multiple treatment sources. The multiple treatment sources can be the same as or different from each other in treatment modality, treatment output capability, as well as other characteristics. The treatment selection device can be electrically coupled to a single treatment delivery device 50' or multiple treatment delivery devices. Each of such treatment delivery devices can have a single treatment delivery member or multiple treatment delivery members. The multiple treatment delivery devices can be the same as or different from each other in the number of treatment delivery members, construction (e.g., size, shape, material composition), configuration, as well as functionalities (e.g., with or without sensors such as thermal sensors, lumens such as infusion as well as cooling and aspiration lumens). The multiple treatment delivery members in a treatment delivery device can be the same as or different from each other in manner of deployment (e.g., direction, curvature, location), construction (e.g., shape, size, material composition), configuration, as well as functionalities (e.g., with or without sensors such as thermal sensors, lumens such as infusation, as well as cooling and aspiration lumens). The treatment volumes provided by the treatment delivery members of the same treatment delivery device or multiple treatment delivery devices can overlap into a desired treatment zone that substantially cover a selected tissue volume targeted for treatment.

Methods disclosed herein include methods of tissue treatment using algorithms grouping different subsets of multiple treatment delivery members or the same subset of the treatment delivery members in different configurations for testing as well as treatment delivery, and methods of using the treatment apparatus disclosed herein for tissue treatment. One exemplary method includes: delivering a treatment modality from a treatment source through a treatment selection device at a first selection setting to a treatment delivery device at a first delivery setting, wherein the treatment selection device comprises multiple selection mechanisms, and the treatment delivery device comprises multiple treatment delivery members; changing the treatment selection device from the first selection setting to a second selection setting; and delivering the treatment modality from the treatment source through the treatment selection device at the second selection setting to the treatment delivery device, such that the treatment delivery device delivers the at least one treatment modality at a second delivery setting. The first and second selections settings can be different in the setting of at least one of the multiple selection mechanisms (e.g., on verses off, positive polarity verses negative polarity). The first and second delivery settings can be different in the setting of at least one of the multiple treatment delivery members (e.g., delivery enabled verses disabled, positive polarity verses negative polarity).

The method of delivery can further include employing a processing circuit to change the treatment selection device from the first selection setting to the second selection setting. The method can further include sensing a change in the delivery of the at least one treatment modality from the treatment source to the treatment delivery device prior to changing the selection setting. The method can further include powering the processing circuit with a power storage device. The method can further include deriving a direct current power from the at least one treatment modality delivered from the treatment source.

One exemplary method of using the tissue treatment apparatus disclosed herein can include: providing a tissue treatment apparatus that includes a treatment delivery device that is electrically coupled to a treatment selection device, wherein the treatment selection device includes multiple selection mechanisms, and the treatment delivery device includes multiple treatment delivery members; placing the treatment delivery device into or adjacent to a target tissue; delivering a treatment modality from a treatment source through the treatment selection device at a first selection setting and through the treatment delivery device at a first delivery setting to the target tissue; changing the treatment selection device from the first selection setting to a second selection setting; and delivering the treatment modality from the treatment source through the treatment selection device at the second selection setting and through the treatment delivery device to the target tissue, such that the treatment delivery device delivers the treatment modality at a second delivery setting. The first and second selections settings can be different in the setting of at least one of the multiple selection mechanisms (e.g., "on" verses "off"). The first and second delivery settings can be different in the setting of at least one of the multiple treatment delivery members (e.g., delivery enabled verses disabled, positive polarity verses negative polarity).

The method of delivery can further include employing a processing circuit to change the treatment selection device from the first selection setting to the second selection setting. The method can further include sensing a change in the delivery of the at least one treatment modality from the treatment source to the treatment delivery device prior to changing the selection setting. The method can further include powering the processing circuit with a power storage device. The method can further include deriving a direct current power from the at least one treatment modality delivered from the treatment source.

As non-limiting examples of control features suitable for the tissue treatment apparatuses disclosed herein, the selection mechanisms allow modes of operation with different characteristics to be combined in any desirable manner. For example, the selection mechanisms can enable the treatment delivery members or subsets thereof running in bipolar mode (e.g., in RF energy delivery, such as for tissue ablation) to be carried out in serial as well as in parallel. Without being limited thereto, it is believed that the bipolar mode is more efficient than the monopolar mode, thereby allowing faster treatment of the tissue between the treatment members (e.g., raising tissue temperature between the electrodes quickly to ablation range). The same selection mechanism can then enable the treatment delivery members or subsets thereof to run in monopolar mode. Monopolar mode is believed to be better in promoting the growth of the treatment volume, allowing a larger treatment volume to be achieved, if desirable.

Figure 9:
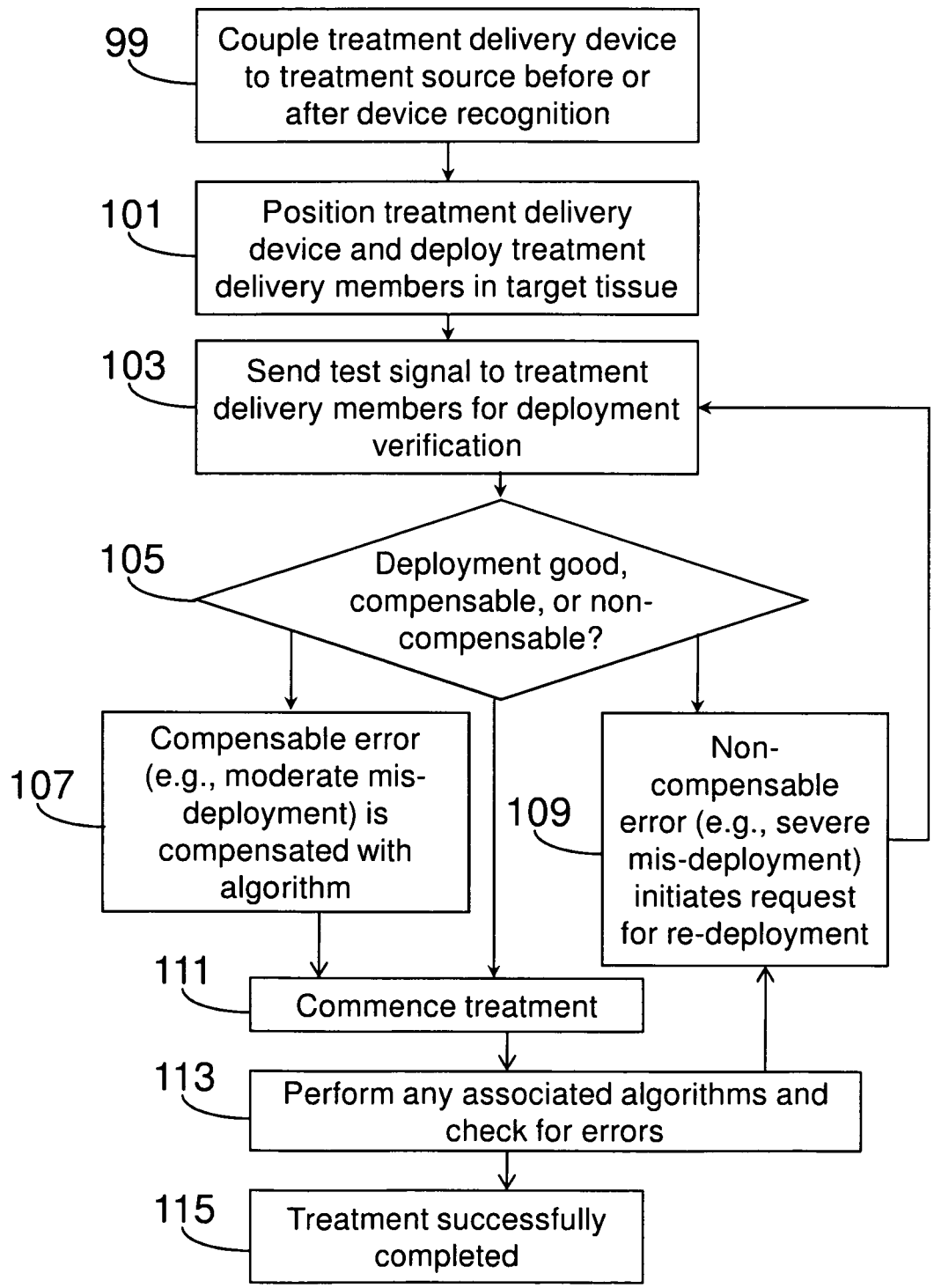
FIG. 9 is a flow chart illustrating algorithms for use with a tissue treatment apparatus according to the present application.

Referring now to FIG. 9, a flow chart is shown to illustrate algorithms for use with a tissue treatment apparatus such that errors in deployment of the treatment delivery members can be determined and corrected. As shown, a treatment delivery device is coupled to the treatment source 99, the delivery device is positioned, and treatment delivery members are deployed in target tissue 101. A test signal is sent to treatment delivery members for deployment verification 103. The status of deployment is then determined as labeled by example categories such as good, compensable or non-compensable 105. A compensable error such as moderate mis-deployment is then compensated by the algorithm 107, treatment is commenced 111, at which time a check for errors can be made by performing any associated algorithms 113 to ensure that the deployment configuration remains within acceptable limits throughout treatment. If there are no errors through treatment, treatment will be successfully completed 115. Alternatively, if deployment is non-compensable (such as severe mis-deployment) or if errors are found in the check for errors during treatment 113, then a request is initiated for redeployment 109, and a test signal is once again sent to treatment delivery members 103. If deployment is subsequently optimal or within compensable limits, treatment can be completed (107-115).

FIGS. 10A-10D show waveforms, respectively, for a voltage level (such as for RF), a detected signal, and data bit to a controller, with FIG. 10D indicating correlating data in binary form. More specifically, FIGS. 10A-10D show how energy can be used to send a signal for communication between the generator and switching mechanisms of the tissue treatment apparatus. FIG. 10A shows a waveform 117 indicating voltage (such as RF voltage) that in one embodiment would be sent from the generator using the same path as for the treatment modality (such as RF administration). The voltage is shown in certain embodiments in bursts of approximately 0.01 to 0.1 second in length of time (though embodiments could be envisioned that are longer, including, but not limited, to twice or three times that range), at 460 KHz and from zero to four volts. FIG. 10B shows a waveform 119 for a detected signal showing voltage from zero to four volts (showing the voltage at a sense line), FIG. 10C depicts a waveform (121) showing data bit to the controller over time, and the binary code (data) is show (FIG. 10D (123)) corresponding to the sent information.

Using this method, standard serial protocols can be used to send messages to the selection mechanisms. Typical non-limiting example messages would be "turn on switch 5," "turn on switch 12," or "turn off all switches." When treatment commences, no signaling is required because the relays are set in the correct clinical position, and treatment (such as RF treatment in one embodiment) is applied to the correct pins. Once the treatment using these pins is over, the voltage sent over the line used to send information from the generator in subclinical "signaling mode" as shown in FIGS. 10A-10D and new commands are sent to the selection mechanisms. In one aspect, in additional embodiments, the selection mechanisms and the generator are capable of communication).

In one aspect, the generator can utilize user input or information gathered from sensors from treatment delivery members for resistance, temperature, time, or other modalities (or time of treatment) to determine when to send a signal to the microprocessors, circuits, and switches involved in altering or changing energy delivery to treatment delivery members in order to change the polarity, pattern of activation (which members are activated at all or what order or for what time), or activation levels of treatment delivery members. Due to the fact the actual switching occurs within the handle of the tissue treatment apparatus, and the fact that the treatment voltage and voltages used to signal changes utilize the same path, there is no need for additional wires. This is a significant advantage over current technologies due to the bulk and complexity necessary to contain extra wiring necessary to communicate similar signals and which could become impractical or unreasonable depending on the apparatus and treatment complexity.

In one aspect, the treatment delivery device, alone or in combination with the treatment selection device, can be configured as a disposable unit to be connected by a user to the treatment source. Recognition of the disposable unit by the treatment source, which can include the identification of one or more of device type (treatment modality designed for), manufacturer, make, model, production date, expiration date, use history, but not limited thereto, can take place before, during, or after the connection. The disposable unit can include a communication device or devices for the recognition process. Non-limiting examples of such communication devices include ID tags (e.g., RFID), transponders, print patterns (e.g., bar code, pixel patterns), and electronic circuits. In particular, recognition can take place during or after connection of the disposable unit to the treatment source when an electric circuit is used as the communication device. Such an electric circuit can be incorporated in the treatment delivery device as well as the treatment selection device as disclosed herein, and can enable one-way communication (e.g., generator reading information from the disposable unit) or two-way communication (e.g., generator write/record information onto memory within the disposable unit, in addition to generator reading information from the disposable unit).

After the disposable unit is connected to the treatment source, and optional disposable unit recognition takes place, the treatment delivery device of the disposable unit can be positioned into or adjacent to a selected target tissue. In one aspect, the target tissue selection as well as the device positioning can involve one or more of biological imaging, such as optical (e.g., laparoscope, endoscope), ultrasound, computer tomography, magnetic resonance, fluoroscopy, and others known to those of ordinary skill in the art.

In one aspect, the treatment source, or an auxiliary electric device, can send one or more testing signals to the multiple treatment delivery members of the treatment delivery device to verify proper positioning as well as deployment. The testing signals can be 10% or less than the energy level used during treatment delivery. The testing signals can be electrical pulses delivered between any two treatment delivery members, and the results (e.g., voltage, current, impedance) can be used to indicate the distances between the treatment delivery members. In one non-limiting example, very low impedances can indicate that the corresponding treatment delivery members are deployed too close together. When only a few (e.g., 2 or 3) treatment delivery members are identified as being mis-deployed, the algorithm can deem such mis-deployment compensable, and can treat the closely deployed treatment delivery members as a single treatment delivery member. That is, the settings of the closely deployed treatment delivery members (e.g., on/off, positive/negative polarity assignment) can be forced by the algorithm to be the same and change together at all times during the procedure following the device placement. In another aspect, when more than a few treatment delivery members are identified as being mis-deployed, the algorithm can deem such mis-deployment severe, and output one or more perceptible signals (e.g., error message on a graphic user interface) to request the user to re-deploy as well as re-position the treatment delivery device. Following such re-positioning as well as re-deployment, the testing is carried out again to verify proper positioning as well as deployment.

When the proper positioning as well as deployment of the treatment delivery device is verified to be acceptable, treatment delivery can be commenced by the user. The treatment delivery algorithm(s) as described herein above can be executed to deliver the desired treatment. Then error checking subroutines can be executed to verify the completeness as well as uniformity of the treatment. Error checking subroutines can be similar to the testing subroutines described herein above for verifying the positioning as well as deployment of the treatment delivery members. If an error is identified, the algorithm can initiate a request to the user for re-positioning as well as redeployment of the treatment delivery device to repeat the procedure, until the error is cleared, thereby ensuring effective treatment is delivered, and treatment is successfully completed. Then the treatment source can be turned off, the treatment delivery device can be retracted and removed from the patient, and any open wound can be dressed properly as needed.

The treatment apparatus of the present application includes the following features, but are not limited thereto. The treatment selection device can be configured to use testing as well as high-intensity therapeutic energy (e.g., RF energy for tissue ablation) from a generator to convert to low-voltage direct current (DC) power. This converted DC power can be used to power circuits within the treatment selection device, including communicating with the processor therein (e.g., microprocessor) and to deliver power to it.

The processor can allow a testing electric pulse to run through all the treatment delivery members to ensure proper deployment thereof, and communicate the results to the generator (e.g., one-way communication). Minor misalignment of the treatment delivery members can be compensated by the algorithm (e.g., treating the misaligned treatment delivery members as a single member), while major misalignment can require the physician to reinsert as well as re-deploy the treatment delivery device. After the treatment delivery members are deployed to satisfaction, the algorithm can have the processor distribute treatment (e.g., therapeutic energy) to the treatment delivery members according to the various sequential groupings instruction in the algorithm that is preprogrammed into the processor. The distribution of treatment can involve the use of selection mechanisms (e.g., latch relays). The number of selection mechanisms in the circuit can depend on the number of treatment delivery members in the treatment delivery device. The algorithm(s) can maximize the volume to time ratio for treating the tissue.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

The invention claimed is:

1. A treatment selection device comprising:
    a treatment delivery device comprising at least a first treatment delivery member and a second treatment delivery member, each to be deployed into tissue to deliver irreversible electroporation (IRE) energy to a target tissue zone;
    a processing circuit programmed to:
    set a plurality of treatment parameters:
    transmit a test signal through at least one of the deployed first treatment delivery member and the deployed second treatment delivery member; and
    determine that the deployed first treatment delivery member or the deployed second treatment delivery member has been mis-deployed prior to treatment based upon a depth of the deployed first treatment delivery member or the deployed second treatment delivery member, and a distance between the deployed first treatment delivery member and the deployed second treatment delivery member; and
    determine a change to at least one of the plurality of treatment parameters to compensate for the mis-deployment of the first treatment delivery member or the second treatment delivery member without withdrawing the deployed first treatment delivery member or deployed second treatment delivery member from the target tissue zone.

2. The treatment selection device of claim 1, wherein the processing circuit is programmed to automatically change the at least one of the plurality of treatment parameters to compensate for the mis-deployment of the first treatment delivery member or the second treatment delivery member.

3. The treatment selection device of claim 1, wherein the processing circuit is programmed to send a message to a display device that indicates that the deployed first treatment delivery member or the deployed second treatment delivery member has been mis-deployed prior to treatment.

4. The treatment selection device of claim 1, wherein the processing circuit is programmed to send a message to a display device that indicates the determined change to at least one of the plurality of treatment parameters to compensate for the mis-deployment of the first treatment delivery member or the second treatment delivery member.

5. The treatment selection device of claim 1, wherein the processing circuit is further programmed to determine the distance between the deployed first treatment delivery member and the deployed second treatment delivery member based upon an impedance measurement from the test signal.

6. A method of treating a tissue of a patient using a treatment delivery device having at least a first treatment delivery member and a second treatment delivery member, each to be deployed into the tissue to deliver irreversible electroporation (IRE), the method comprising:
    piercing the tissue with the first treatment delivery member and the second treatment delivery member so as to deploy the first treatment delivery member and the second treatment delivery member;
    applying at least one test signal through at least one of the deployed first treatment delivery member and the deployed second treatment delivery member;
    determining, based on the applied test signal, that the deployed first treatment delivery member or the deployed second treatment delivery member has been mis-deployed prior to treatment based upon a depth of the deployed first treatment delivery member or the deployed second treatment delivery member, and a distance between the deployed first treatment delivery member and the deployed second treatment delivery member; and
    determining a change to at least one of a plurality of treatment parameters to compensate for the mis-deployment of the first treatment delivery member or the second treatment delivery member without withdrawing the deployed first treatment delivery member or the deployed second treatment delivery member from the tissue.

7. The method of claim 6, further comprising:
    automatically changing the at least one of the plurality of treatment parameters while the treatment delivery member is deployed in the tissue.

8. The method of claim 7, wherein the step of automatically changing includes changing one or more of a treatment energy voltage, treatment energy duration, electrical polarity, output power level, combination of treatment delivery members, and number of treatment energy pulses.

9. The method of claim 6, further comprising sending a message to a display device that indicates that the deployed first treatment delivery member or the deployed second treatment delivery member has been mis-deployed prior to treatment.

10. The method of claim 9, further comprising sending a message to a display device that contains the determined change to at least one of the plurality of treatment parameters to compensate for the mis-deployment of the first treatment delivery member or the second treatment delivery member.

11. The method of claim 6, wherein wherein the step of piercing the tissue includes deploying the first treatment delivery member and the second treatment delivery member from within the treatment delivery device.

12. The method of claim 6, wherein determining the distance between the deployed first treatment delivery member and the deployed second treatment delivery member is based upon an impedence measurement from the test signal.

13. A treatment selection device comprising:

a treatment delivery device comprising a longitudinal shaft and at least two treatment delivery members to be deployed into tissue to delivery irreversible electroporation (IRE) energy to a target tissue zone;

wherein the at least two treatment delivery members are deployed radially outwardly from the longitudinal shaft of the treatment delivery device into the target tissue zone; and a processing circuit programmed to:

set a plurality treatment parameters; transmit at least one test signal through the at least two deployed treatment delivery members; and determine that at least one of the least two deployed treatment delivery members has been mis-deployed prior to treatment based upon a depth of the least two treatment delivery members and a distance between the at least two treatment delivery members; and determine a change to at least one of the plurality of treatment parameters to compensate for the mis-deployment of at least one of the least two deployed treatment delivery members without withdrawing the at least two treatment delivery members from the target tissue zone.

14. The treatment selection device of claim 13, wherein:

the processing circuit is further programmed to determine the distance between the at least two treatment delivery members based upon an impedance measurement from the test signal.

* * * * *